US00PP14749P2

(12) United States Plant Patent

Anderson et al.

(10) Patent No.: US PP14,749 P2

(45) Date of Patent: May 4, 2004

(54) CHRYSANTHEMUM PLANT NAMED 'MN90-275-27'

(50) Latin Name: *Chrysanthemum morifolium*
Varietal Denomination: MN90-275-27

(75) Inventors: Neil Anderson, St. Paul, MN (US); Peter Ascher, Bowler, WI (US)

(73) Assignee: University of Minnesota, Minneapolis, MN (US)

( * ) Notice: Subject to any disclaimer, the term of this patent is extended or adjusted under 35 U.S.C. 154(b) by 0 days.

(21) Appl. No.: 09/999,620

(22) Filed: Oct. 30, 2001

(51) Int. Cl.[7] ..... A01H 5/00

(52) U.S. Cl. ..... Plt./289

(58) Field of Search ..... Plt./289

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP9,445 | P | 1/1996 | VandenBerg |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Peter Ascher, et al., "Maxi–Mums A Horticultural Breakthrough!" Minnesota Report 242–1997 University of Minnesota, Distribution Center Publication MR–67280B Minnesota Agricultural Experiment Station, University of Minnesota (1997).

R.B. Clark, History of Culture of Hardy Chrysanthemums, National Crysanthemum Society 18(3):144 (1962).

W.W. Garner, et al., Flowering and Fruiting of Plants as Controlled by the Length of Day, 1920, p. 377–400, Yearbook of the Department of Agriculture, 1920 USA.

Peter Ascher, et al., Breeding and New Cultivars, Academic Perspective, Tips on Growing and Marketing Garden Mums, Ohio Florists Association 1996.

Bradford Bearce et al., Chrysanthemums A Manual of the Culture, Diseases, Insects and Economics of Chrysanthemums, Jun. 1964, pp. 6–19, Prepared for The New York State Extension Service Chrysanthemum School with the Cooperation of the New York State Flower Growers Association, Inc.

Neil O. Anderson, et al., Rapid Generation Cycling of Chrysanthemum Using Laboratory Seed Development and Embryo Rescue Techniques, Journal of the American Society of Horticultural Science, Mar. 1990, pp. 329–336, vol. 115(2), Alexandria, Virginia 22314.

Leon Glicenstein, Breeding and New Cultivars, Commercial Perspective, Tips on Growing and Marketing Garden Mums, Ohio Florist's Association 1996.

M.A. Nazeer, et al., Cytogenetical Evolution of Garden Chrysanthemum, Current Science, Jun. 20, 1982, vol. 51, No. 12.

Edward Higgins, Containers and Marketing, Tips on Growing and Marketing Garden Mums, Ohio Florists Association 1996.

Ernest L. Scott, The Breeder's Handbook, 1957, pp. 1–76 Handbook No. 4, National Chrysanthemum Society, Inc., USA.

John Woolman, Chrysanthemums for Garden and Exhibition, 1953, pp. 1–103, W.H. & L. Collingridge Ltd., Tavistock Street, London WC2 and Transatlantic Arts Incorporated, Forest Hills, New York.

H.G. Witham Fogg, Chrysanthemum Growing, 1962, pp. 171, John Gifford Limited, London, W.C.2.

National Agricultural Statistics Service, USDA Additional Floriculture Information, pp. 1–84, National Agricultural Statistics Service, Floriculture Crops, 1998 Summary, Jun. 1999.

Handbook on Chrysanthemum Classification, A Publication of the Classification Committee National Chrysanthemum Society, Inc., U.S.A., 1996 Edition.

C. Ackerson, Chap. 12, Development of the Chrysanthemum in China, pp. 146–155, National Chrysanthemum Society Bulletin 1967.

C. Ackerson, Chapter 11, Original Species of the Chrysanthemum, pp. 105–107, National Chrysanthemum Society Bulletin, 1967.

G.J. Dowrick, The Chromosomes of Chrysanthemum 1: The Species, *Heredity*, 6:365–375 (1952).

Junyu, C., et al., *Acta Horticulturae*, 404:30–36 (1995).

*Primary Examiner*—Bruce R. Campell
*Assistant Examiner*—W. C. Haas
(74) *Attorney, Agent, or Firm*—Wood, Phillips, Katz, Clark & Mortimer

(57) ABSTRACT

A new and distinct Chrysanthemum plant named 'MN90-275-27' is provided.

4 Drawing Sheets

Latin name of the genus and species of plant claimed: *Chrysanthemum morifolium.*

Variety denomination: 'MN90-275-27'.

BACKGROUND OF THE INVENTION

The present invention comprises a new and distinctive chrysanthemum plant, hereinafter referred to by the cultivar name 'MN90-275-27'. The breeding program which resulted in the production of the new cultivar was carried out at St. Paul, Minn. In 1978, variety '77-4M3-7, a *Dendranthema×grandiflora*, a proprietary selection of the University of Minnesota breeding program, was selfed and the resulting seeds collected and planted. From the plants grown from the seeds, one line, identified as '79-Z142-2' (unpatented) was selected. In 1981, variety 77-4M2-7' was selfed again and the resulting seeds collect and planted. '77-4M2-7' has the following characteristics: (a) the plant habit is upright; (b) the plant dimensions are that the plant has a diameter of about 18–20 inches tall by 12–14 inches wide; (c) the plant is hardy in zones 4–10 (west); (d) the flower of the plant is semi-double quill/spoon, yellow/bronze intensification under cooler temperatures; (e) the plant has leaves that are dark green in color, that are deeply raised; and (f) the plant is early season (6 weeks short day (hereinafter "SD" response group). From the plants grown from this seed, one line, identified as '82-124-3', (unpatented) was selected. In 1985, a cross was made between '79-Z142-2', as the female parent and '82-124-3' as the male parent. The resulting seeds were collected. In 1986, seedlings from this cross were grown and flowering progeny evaluated. Seedling '86-135-38' (unpatented) was selected and crossed as the female parent with 'Patriot' as the male parent in 1989. The male or pollen parent of 'MN90-275-27' was 'Patriot' cultivar (U.S. Plant Pat. No. 3,897) was commercially available from Yoder Brothers, Inc., Barberton, Ohio up until 1995 (when it was replaced by the variety known as 'Nicole' (U.S. Plant Pat. No. 7,507) and has the following characteristics: (a) the plant habit is cushion; (b) the plant dimensions are that the plant is 16–18 inches tall by 14–16 inches wide; (c) the plant is hardy in zones 6–10 (west); (d) the flower is white and decorative; (e) the plant has leaves that are dark green and deeply incised; and (f) the plant is in a 7 day SD response group. The resulting seed was collected. In 1990, seedlings from this cross were grown, flowering progeny evaluated, and seedling 'MN90-275-27' selected. The parentage of the new cultivar can be summarized as follows:

'86-135-38' (female)×'Patriot' (male)

Asexual reproduction of the new cultivar by terminal or stem cuttings taken 1990 through 2000 at St. Paul, Minn., U.S.A. has demonstrated that the characteristics of the new cultivar as herein described are firmly fixed and are retained through successive generations of such asexual propagation.

SUMMARY OF THE INVENTION

It was found that the cultivar of the present invention:

(a) exhibits a prostrate-type and massive floral display during its first and/or second year of growth;

(b) winter hardiness in zones 3–10;

(c) frost tolerant flowers in zones 3–10; and (d) exhibits self-pinching.

The 'MN90-275-27' cultivar has not been observed under all possible environmental conditions to date. Accordingly, it is possible that the phenotype may vary somewhat with variations in the environment, such as temperature, light intensity, and day length.

When the new cultivar of the present invention is compared to the Chrysanthemum plant named 'Lisa' (U.S. Plant Pat. No. 8,992), it is found to exhibit a more spreading and prolific habit accompanied with a massive floral display in its second and subsequent years after planting. Reference is made to Table A below which compares certain characteristics of 'MN90-275-27' to the Chrysanthemum plant named 'Lisa' (U.S. Plant Pat. No. 8,992).

TABLE A

| CHARACTERISTIC | MN90-275-27 | 'Lisa' |
|---|---|---|
| Plant Shape | prostrate | cushion |
| Plant height | | |
| (1st year) | 0.25' | 1.0–1.5' |
| (2nd year) | 0.5' | -(dead) |
| Flowering response # weeks short days (SD) | 7.0 | 7.0 |
| Flower Type | Decorative, Double | Decorative, Double |
| Flower Diameter | 6.0 cm | 6.0–7.0 cm |
| Ray florets, color, mature | | |
| Adaxial surface | RHS Yellow Group 5B | RHS Yellow Group 5B |
| Abaxial surface | RHS Yellow Group 5C | RHS Yellow Group 5B |

BRIEF DESCRIPTION OF THE PHOTOGRAPHS

The accompanying photographs show as nearly true as it is reasonable possible to make the same in color illustrations of this type, typical flower and foliage characteristics of the new cultivar. The plants were grown in a greenhouse as St. Paul, Minn., USA.

D TAILED BOTANICAL DESCRIPTION

Figure 1:
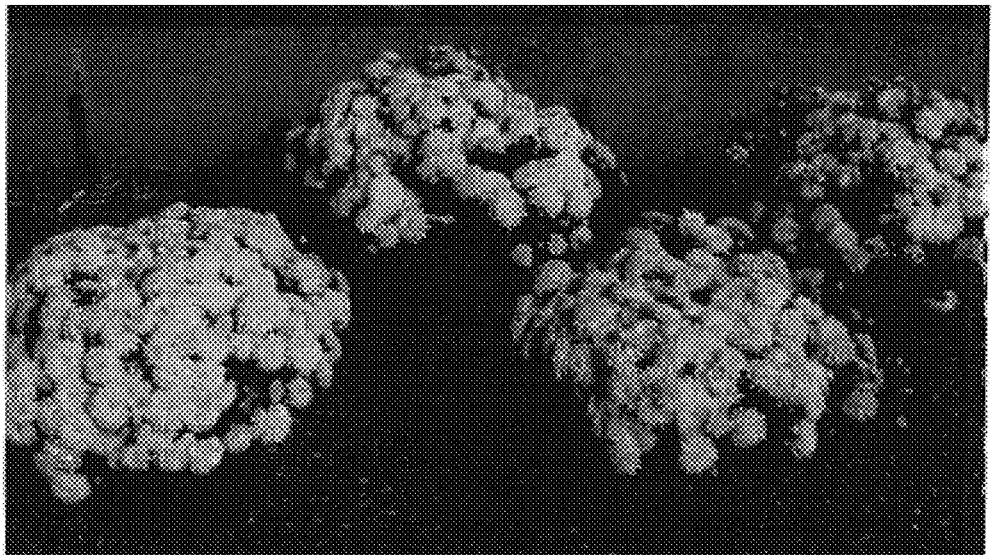
FIG. 1 is a color photograph of chrysanthemum variety 'MN90-275-27' after one year of growth.
Figure 2:
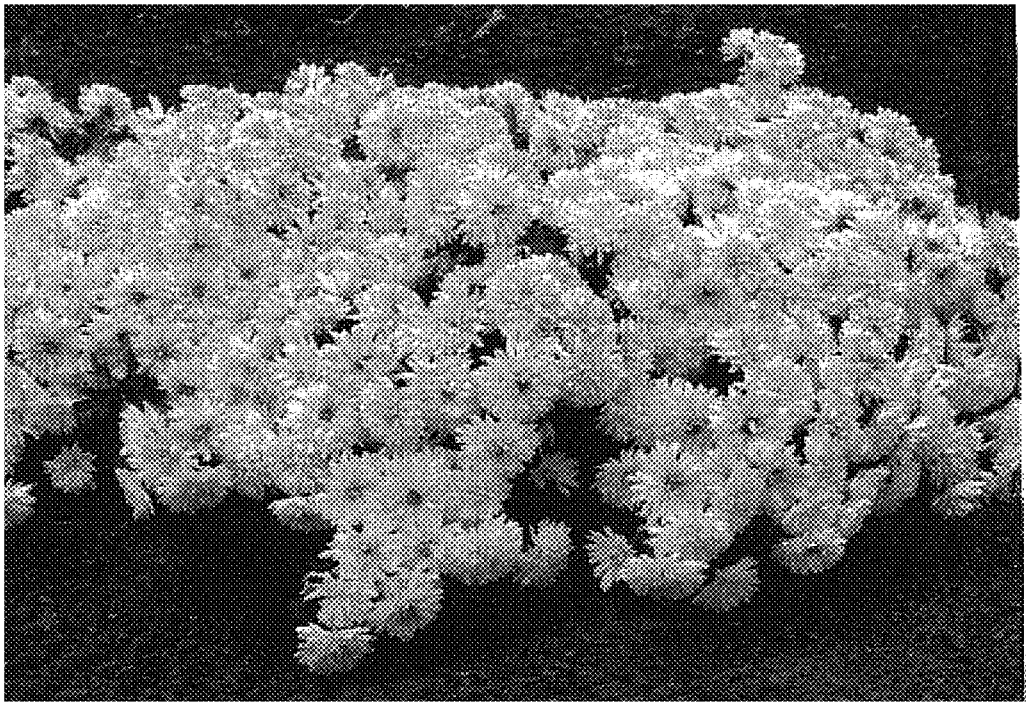
FIG. 2 is a color photograph of chrysanthemum variety 'MN90-275-27' after two years of growth.
Figure 3:
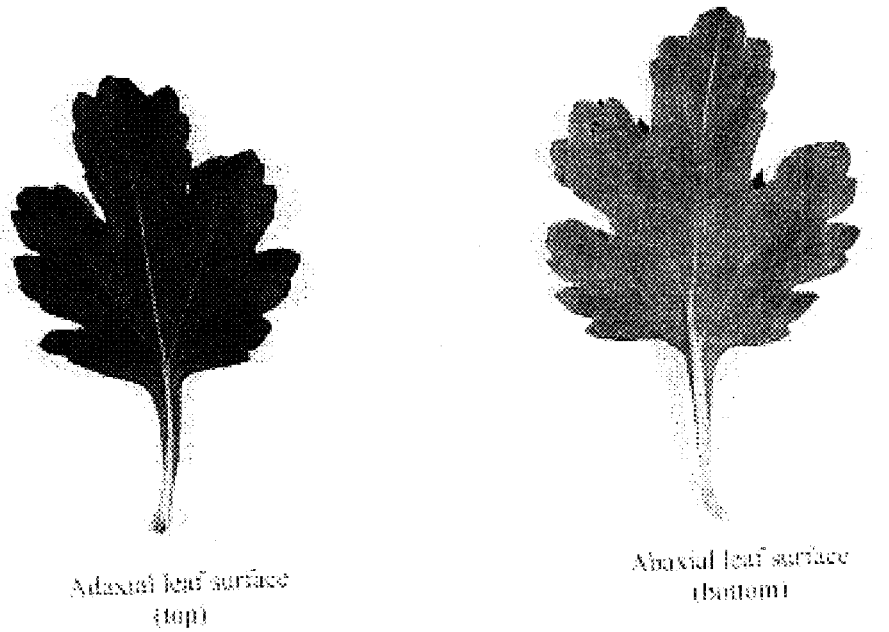
FIG. 3 shows an adaxial and abaxial view of the leaf shape of chrysanthemum variety 'MN90-275-27'.
Figure 4:
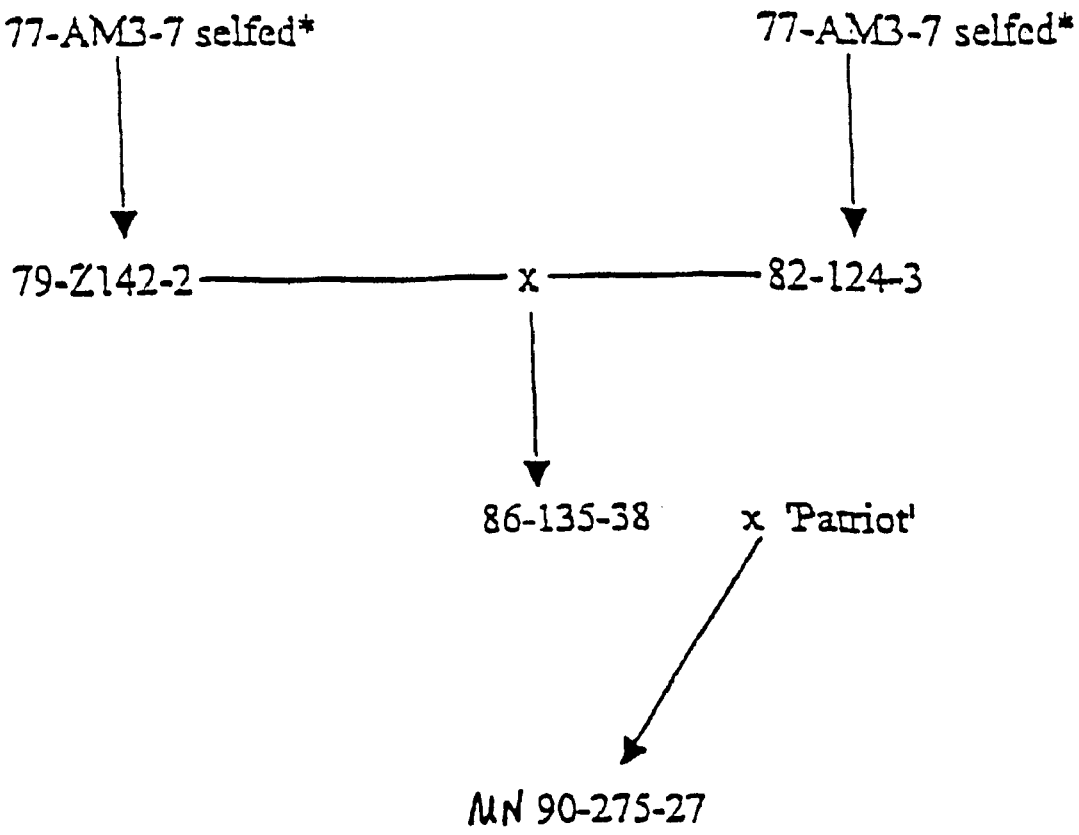
FIG. 4 shows the breeding history of chrysanthemum variety 'MN90-275-27'.

The chart used in the identification of colors descried herein is The R.H.S. Colour Chart of The Royal Horticultural Society, London, England (1995 Edition). The color values were determined on Jan. 18, 2001 in St. Paul, Minn. The readings were taken between 1:00 and 3:00 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during night. The plants used for the below description were approximately ten (10) weeks old.

Propagation:

*Type.*—Herbaceous stem cutting.

*Time to rooting.*—About 1 week.

*Root description.*—Numerous fine roots.

Plant description:

*Appearance, shape.*—Flat.

*Appearance, growh habit.*—Prostrate.

*Appearance, growth rate/vigor.*—Vigorous.

*Plant height.*—About 0.25' feet (first year). About 0.5' feet (second year).

*Lateral branch length.*—5–28 cm.

*Quantity of lateral branches after removal of apical meristem.*—One per node.
*Stem color.*—RHS Yellow-Green Group 146C.

Foliage description:
*Number of leaves per plant.*—About 1,000.
*Number of leaves per lateral branch.*—About 20.
*Leaf arrangement.*—Alternate.
*Leaf size, fully expanded, length.*—8.9 cm.
*Leaf size, fully expanded, width.*—6 cm.
*Leaf apex.*—Mucronulate.
*Leaf base.*—Cuneate.
*Leaf margin.*—Incised-Mulberry-like incusions.
*Leaf texture.*—Glabrous.
*Petiole length.*—3.3 cm.
*Color, young foliage adaxial surface.*—RHS Green-Group 137C.
*Color, young foliage abaxial surface.*—RHS Greyed-Green Group 191A.
*Color, fully expanded foliage adaxial surface.*—RHS Green-Group 137B.
*Color, fully expanded foliage abaxial surface.*—RHS Yellow-Green Group 147B.
*Color, venation adaxial surface.*—RHS Greyed-Green Group 191A.
*Color, venation abaxial surface.*—RHS Yellow-Green Group 147B.
*Color, petiole.*—RHS Yellow-Green Group 147B.

Phyllary description:
*Appearance.*—The involucral bracts (phyllaries) are crenulate with entire margins.
*Color.*—RHS Green Group 139C.
*Texture.*—Glabrous.
*Size.*—Approximately 0.2–0.4 cm in length.

Inflorescence description:
*Appearance.*—Head (composite).
*Flowering response.*—7 weeks (SD).
*Quantity of inflorescences.*—About 100 (first year).
*Inflorescence size, diameter.*—6 cm.
*Inflorescence size, depth (height).*—2 cm.
*Inflorescence size, diameter of disc.*—0.3 cm.
*Opening inflorescences, bud shape.*—Flattened, inverted ball.
*Opening inflorescences, bud size, length.*—1.1 cm.
*Opening inflorescences, bud size, width.*—2.2 cm.
*Opening inflorescences, bud color.*—RHS Yellow Group 7A.
*Ray florets, shape.*—Spatulate.
*Ray florets, size, length.*—2.7 cm.
*Ray florets, size, width.*—0.7 cm.
*Ray florets, apex.*—Denate with 1–4 teeth, often deeply cleft.
*Ray florets, base.*—Attenuate.
*Ray florets, margin.*—Entire.
*Ray florets, texture.*—Glabrous.
*Ray florets, aspect.*—Upright (center) to reflexed (outer).
*Number of ray florets per inflorescence.*—About 206.
*Ray florets, color, when opening, adaxial surface.*—RHS Yellow Group 6A.
*Ray florets, color, when opening, abaxial surface.*—RHS Yellow Group 6B.
*Ray florets, color, mature, adaxial surface.*—RHS Yellow Group 5B.
*Ray florets, color, mature, abaxial surface.*—RHS Yellow Group 5C.
*Ray florets, color, fading to.*—RHS Yellow Group 2C.
*Disc florets, shape.*—Tubular.
*Disc florets, size, length.*—0.4 cm.
*Disc florets, size, width.*—0.1 cm.
*Number of disc florets per inflorescence.*—About 7.
*Ray florets, color, immature.*—RHS Yellow-Green Group 154A.
*Ray florets, color, mature.*—RHS Green-Yellow 1A.
*Peduncle, aspect, strength.*—Intermediate.
*Peduncle, aspect, angle to stem.*—45°.
*Peduncle, length, first peduncle.*—1.8 cm.
*Peduncle, length, fourth peduncle.*—2.5 cm.
*Peduncle, texture.*—Pubesent.
*Peduncle, color.*—RHS Yellow-Green Group 144A.
*Reproductive organs, androecium, floret location.*—Disc florets.
*Anther color.*—RHS Yellow-Green Group 1A.
*Pollen, abundance.*—Little.
*Pollen, color.*—RHS Yellow-Orange Group 14A.
*Reproductive organs, gynoecium, floret location.*—Disc/ray florets.
*Style color.*—RHS Yellow-Green Group 154B.
*Stamen description.*—Stamens are located within each individual disk floret. Each stamen is borne on a filament that, when mature (dehiscent with pollen shedding longitudinally along the long axis of the anther), places the stamens above the stigma (i.e., the top portion of the pistil (there are approximatley 60 per inflorescence). Likewise, each disk floret also possesses a pistil (there are approximately 191 per inflorescence). Therefore, the total number of pistils/inflorescence is 251 (60+191). The size of the pistil (length) is approximately 1 cm.
*Disease resistance.*—None Known as 'MN90-275-27' has not been tested for any diseases.
*Seed production and fruit.*—About 212 ovules/flower. The fruit is an achene, a dry, indehiscent fruit with a single locule and a single seed, and with the seed attached to the ovary wall at a single point. The achene does not have any pappus of awns for bristles; its general shape is a half-inflated football oval with pointed ends. Seed size is about 0.2–0.5 cm in length and about 0.1–0.2 cm in width. The surface texture is ridged. The color designation for the seed is RHS Brown Group 200D.
*Fragrance.*—Fragrance is noticeable when handling or bruising the foliage.

What is claimed is:

1. A new and distinct chrysanthemum plant as herein described and illustrated.

* * * * *

90-275-27